United States Patent
Robinson

(10) Patent No.: US 9,974,527 B2
(45) Date of Patent: *May 22, 2018

(54) SHAPED CIRCUIT BOARDS SUITABLE FOR USE IN ELECTROSURGICAL DEVICES AND ROTATABLE ASSEMBLIES INCLUDING SAME

(71) Applicant: COVIDIEN LP, Mansfield, MA (US)

(72) Inventor: William E. Robinson, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 468 days.

This patent is subject to a terminal disclaimer.

(21) Appl. No.: 14/691,658

(22) Filed: Apr. 21, 2015

(65) Prior Publication Data

US 2015/0223789 A1    Aug. 13, 2015

Related U.S. Application Data

(63) Continuation of application No. 12/731,247, filed on Mar. 25, 2010, now Pat. No. 9,023,032.

(51) Int. Cl.
*A61B 18/14* (2006.01)
*A61B 17/00* (2006.01)
(Continued)

(52) U.S. Cl.
CPC .............. *A61B 17/00* (2013.01); *A61B 18/14* (2013.01); *A61B 18/1445* (2013.01); *A61B 2017/00017* (2013.01); *A61B 2017/00367* (2013.01); *A61B 2018/0063* (2013.01); *A61B 2018/00577* (2013.01); *A61B 2018/00589* (2013.01); *A61B 2018/00595* (2013.01);
(Continued)

(58) Field of Classification Search
CPC .. A61B 2018/0091; A61B 2018/00916; A61B 2018/00922; A61B 2018/00928; A61B 2018/00952
See application file for complete search history.

(56) References Cited

U.S. PATENT DOCUMENTS 3,648,001 A    3/1972  Anderson et al.
3,801,766 A  *  4/1974  Morrison, Jr. ..... A61B 18/1402
                                              200/275
(Continued)

FOREIGN PATENT DOCUMENTS

WO    2007070919 A1    6/2007
WO    2007089876 A2    8/2007

OTHER PUBLICATIONS

European Office Action dated Jul. 28, 2016, issued in EP Application No. 11 159 769.

(Continued)

*Primary Examiner* — Ronald Hupczey, Jr.

(57) ABSTRACT

An electrosurgical instrument includes a housing having an elongated shaft extending therefrom and a rotatable member disposed on the housing and operably connected to the elongated shaft. The elongated shaft defines a longitudinal axis extending therealong. The rotatable member is configured to rotate the elongated shaft about the longitudinal axis upon actuation thereof. The rotatable member includes an inner surface defining an interior space therein configured to house at least one printed circuit board about the elongated shaft.

20 Claims, 10 Drawing Sheets

(51) Int. Cl.
 *A61B 18/00* (2006.01)
 *A61B 18/18* (2006.01)
(52) U.S. Cl.
 CPC .......... *A61B 2018/00601* (2013.01); *A61B 2018/00916* (2013.01); *A61B 2018/1861* (2013.01)

(56) References Cited

U.S. PATENT DOCUMENTS

| | | | |
|---|---|---|---|
| 4,034,761 A | 7/1977 | Prater et al. | |
| 4,427,006 A | 1/1984 | Nottke | |
| 4,492,832 A | 1/1985 | Taylor | |
| 4,823,791 A | 4/1989 | D'Amelio et al. | |
| 5,275,166 A | 1/1994 | Vaitekunas et al. | |
| 5,312,327 A | 5/1994 | Bales et al. | |
| 6,214,001 B1 * | 4/2001 | Casscells | A61B 17/32002 606/180 |
| 6,500,169 B1 | 12/2002 | Deng | |
| 6,809,508 B2 | 10/2004 | Donofrio | |
| 6,977,495 B2 | 12/2005 | Donofrio | |
| 7,367,975 B2 | 5/2008 | Malecki et al. | |
| 7,674,262 B2 * | 3/2010 | Sugita | A61B 18/1492 606/41 |
| 7,722,607 B2 | 5/2010 | Dumbauld et al. | |
| 7,846,155 B2 | 12/2010 | Houser et al. | |
| 8,022,327 B2 | 9/2011 | Blomeyer | |
| 8,319,134 B2 | 11/2012 | Blomeyer | |
| 9,023,032 B2 * | 5/2015 | Robinson | A61B 18/14 606/41 |
| 2006/0084973 A1 | 4/2006 | Hushka | |
| 2007/0156139 A1 | 7/2007 | Schechter et al. | |
| 2007/0287999 A1 | 12/2007 | Malecki et al. | |

OTHER PUBLICATIONS

European Search Report for European Application No. 11159769 dated Aug. 22, 2011.

* cited by examiner

SHAPED CIRCUIT BOARDS SUITABLE FOR USE IN ELECTROSURGICAL DEVICES AND ROTATABLE ASSEMBLIES INCLUDING SAME

CROSS REFERENCE TO RELATED APPLICATION

This application is a continuation of and claims the benefit of, and priority to, U.S. patent application Ser. No. 12/731,247, filed on Mar. 25, 2010, now U.S. Pat. No. 9,023,032, the entire contents of which are hereby incorporated by reference.

BACKGROUND

1. Technical Field

The present disclosure relates to electrosurgical devices and, more particularly, to shaped printed circuit boards suitable for use in electrosurgical devices and rotatable assemblies including the same.

2. Discussion of Related Art

Printed circuit boards (PCBs), sometimes referred to as printed wiring boards (PWBs) or etched wiring boards, are widely used in the assembly of discrete electrical components into operating circuits. PCBs are available in a variety of different types.

PCBs are generally used to mechanically support and electrically connect electronic components using electrically-conductive pathways or traces that conduct signals on the PCB. A typical PCB includes one or more layers of insulating material upon which patterns of electrical conductors are formed. The insulating layers are generally configured to resist or substantially resist the flow of electricity and to provide physical support for, among other things, conductive layers and electrical components. In addition to conductive traces on the PCB, a patterned array of holes may be formed to allow for layer-to-layer interconnections between various conductive features.

PCBs may have circuits that perform a single function or multiple functions. A typical PCB may include a variety of electrical components. The electrical components are typically processors, memory devices, clock generators, resistors, cooling units, capacitors, light-emitting diodes (LEDs) or other types of electrical components. A PCB on which electrical components are mounted is sometimes referred to as a printed circuit assembly (PCA) or a printed circuit board assembly (PCBA).

PCBs may be generally classified into single-sided PCBs, double-sided PCBs and multi-layer PCBs according to the number of circuit pattern surfaces. PCBs may employ a broad range of technologies to support the electrical components (e.g., through-hole, surface-mount, mixed-technology, components mounted on one or both sides, etc.) and may include a wide range of single or multilayer constructions (e.g., single-sided, double-sided, multilayer, flexible, rigid-flex, stripline, etc).

Electrical signals may be used on PCBs for controlling and/or monitoring the delivery of electromagnetic energy from an energy source to an energy applicator for applying electromagnetic radiation to heat, ablate, cut and/or coagulate tissue. Electrosurgical forceps that employ PCBs may utilize both mechanical clamping action and electrical energy to effect hemostasis by heating the tissue and blood vessels to coagulate, cauterize and/or seal tissue.

Various kinds of electrosurgical devices that employ PCBs have become thin and/or compact. In some devices, the amount of space needed to accommodate the PCBs may make it difficult to reduce the size of the devices. In some cases, PCB layouts large enough to accommodate the electrical components needed to provide desired functionality and/or performance may increase the overall size of the device and potentially hinder usability.

SUMMARY

The present disclosure relates to an electrosurgical instrument including a housing having an elongated shaft extending therefrom and a rotatable member disposed on the housing and operably connected to the elongated shaft. The elongated shaft defines a longitudinal axis extending therealong. The rotatable member is configured to rotate the elongated shaft about the longitudinal axis upon actuation thereof. The rotatable member includes an inner surface defining an interior space therein configured to house one or more printed circuit boards about the elongated shaft.

The present disclosure also relates to an electrosurgical instrument including a housing having an elongated shaft extending therefrom. The elongated shaft includes a proximal end portion and a laterally-oriented slot disposed in the proximal end portion. A rotatable assembly disposed on the housing and operably connected to the elongated shaft. The rotatable assembly includes one or more protrusions configured to engage the slot disposed in the proximal end portion of the elongated shaft. The rotatable assembly also includes a rotatable member and one or more printed circuit boards disposed within the rotatable member about the elongated shaft.

The present disclosure also relates to a rotatable assembly suitable for use in electrosurgical devices including a housing having an elongated shaft extending therefrom, the elongated shaft defining a longitudinal axis extending therealong. The rotatable assembly includes a rotatable member operably connected to the elongated shaft. The rotatable member includes an inner surface defining an interior space therein configured to house one or more printed circuit boards about the elongated shaft.

BRIEF DESCRIPTION OF THE DRAWINGS

Objects and features of the presently-disclosed shaped printed circuit boards and rotatable assemblies including the same will become apparent to those of ordinary skill in the art when descriptions of various embodiments thereof are read with reference to the accompanying drawings, of which.

DETAILED DESCRIPTION

Figure 1:
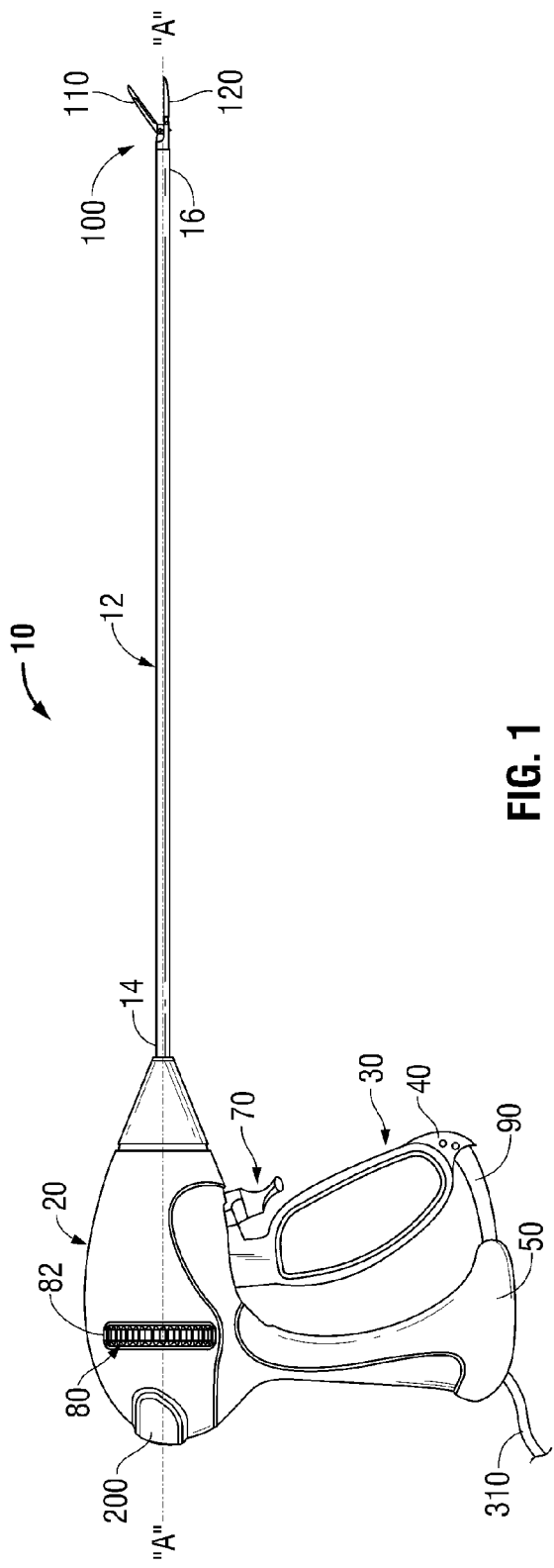
FIG. 1 is a left, side view of an endoscopic bipolar forceps showing a housing, a rotatable member, a shaft and an end effector assembly according to an embodiment of the present disclosure.

Hereinafter, embodiments of the presently-disclosed shaped printed circuit boards and rotatable assemblies including the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As it is used in this description, "printed circuit board" (or "PCB") generally refers to any and all systems that provide, among other things, mechanical support to electrical components, electrical connection to and between these electrical components, combinations thereof, and the like. For the purposes herein, the term "printed circuit board" is interchangeable with the term "printed wiring board" and either is represented herein by the acronym PCB. The PCBs described herein may include electrical components. In general, the term "printed circuit board" is interchangeable, in this disclosure, with the terms "printed circuit assembly" and "printed circuit board assembly". The "PCBs" and "circuit boards" described herein are not limited to electrical component-populated boards, but also include non-populated circuit traced substrates of all types.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another.

Various embodiments of the present disclosure provide a rotatable assembly configured with one or more shaped PCBs. The presently-disclosed shaped PCBs may have a generally circular shape (e.g., PCBs 565 and 566 shown in FIG. 5), a generally half-circular shape (e.g., PCBs 360a, 360b, 361a and 361b shown in FIG. 3A), or other shapes (e.g., PCBs 965 and 1065 shown in FIGS. 9 and 10, respectively). The shaped PCBs described herein may be manufactured from a wide range of materials including FR4 (flame retardant 4) and polyamide base laminated materials. In embodiments, one or more shaped PCBs may be rigid, such as those having a substrate made of alumina or FR-4 glass/epoxy laminate. In embodiments, one or more shaped PCBs may be relatively flexible, such as those having a substrate made of polyimide, polyester, and the like. In embodiments, one or more shaped PCBs (e.g., 965 shown in FIG. 9) may be adapted to releasably engage with embodiments of the presently-disclosed rotatable assembly.

Figure 3A:
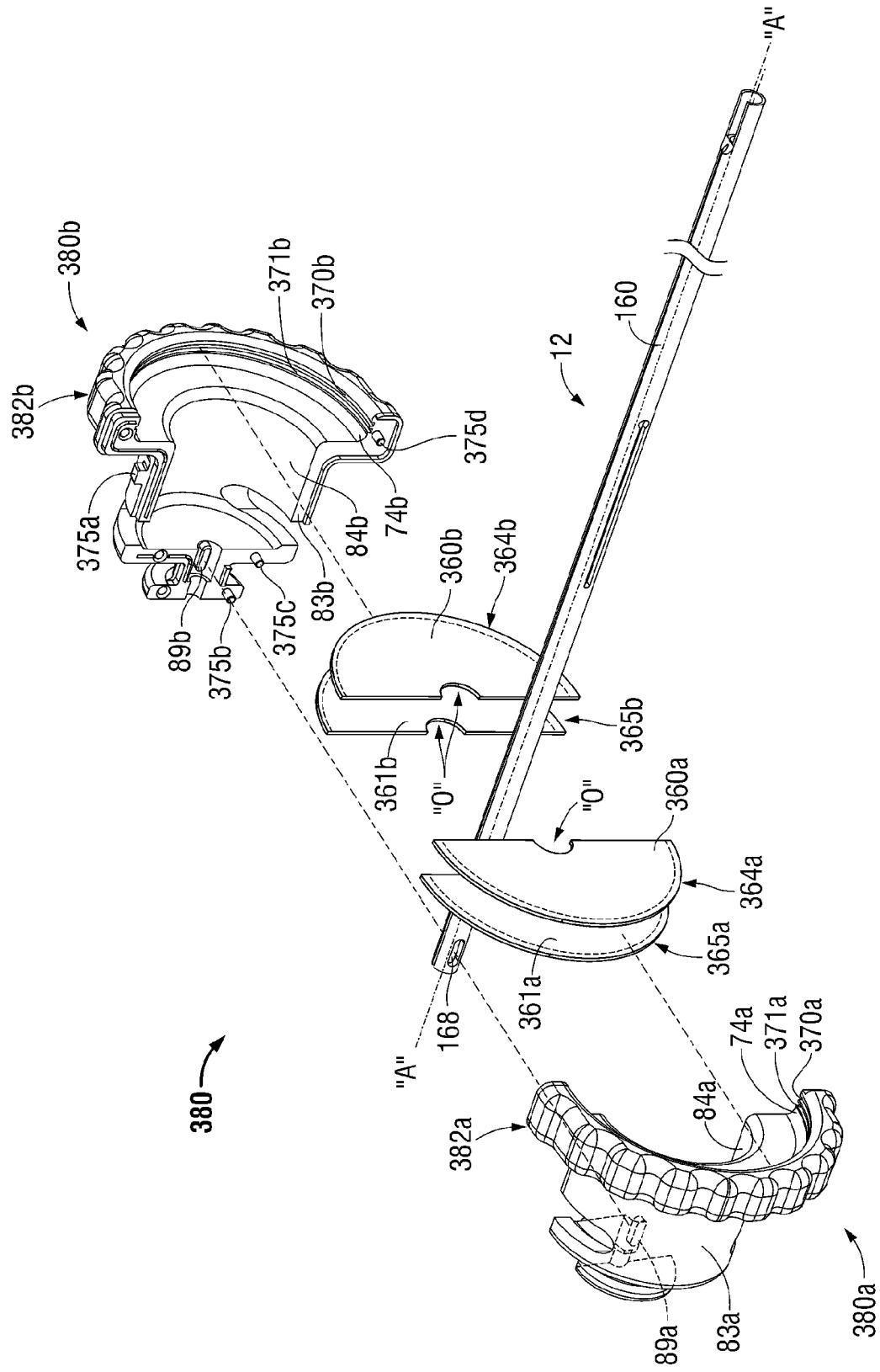
FIG. 3A is an enlarged, perspective view of a rotatable assembly with parts separated according to an embodiment of the present disclosure.

Various embodiments of the presently-disclosed rotatable assembly include a generally circular rotatable member, and may include a substantially hollow body coupled to the rotatable member. The presently-disclosed rotatable assembly according to embodiments may include one or more receptacle assemblies (e.g., 581 shown in FIG. 5) and/or grooves (e.g., 370a shown in FIG. 3A) and/or slots (e.g., 773b shown in FIG. 7) recessed into, or otherwise associated with, inner surfaces of the rotatable member and/or the hollow body. In embodiments, the presently-disclosed receptacle assemblies, grooves and/or slots associated with inner surfaces of the rotatable member and/or the hollow body may be configured to receive therein a portion, e.g., a peripheral edge portion (e.g., 364a shown in FIG. 3A and 564 shown in FIG. 5) or a protruding tab (e.g., "T" shown in FIGS. 7 and 8), of one or more shaped PCBs. In embodiments, the presently-disclosed rotatable assembly may be adapted to releasably house one or more shaped PCBs.

Various embodiments of the presently-disclosed rotatable assembly configured with one or more shaped PCBs may be suitable for use in wired and/or wireless devices. Although the following description describes the use of an endoscopic bipolar forceps, the teachings of the present disclosure may also apply to a variety of electrosurgical devices that include an interior space within a rotatable component, e.g., clamping devices, such as electrosurgical forceps and surgical staplers with jaw clamping mechanisms, and devices utilizing electromagnetic radiation to heat, ablate, cut, coagulate, cauterize and/or seal tissue.

In FIG. 1, an embodiment of an endoscopic bipolar forceps 10 is shown for use with various surgical procedures and generally includes a housing 20, a handle assembly 30, a rotatable assembly 80, a trigger assembly 70, a shaft 12 and an end effector assembly 100, which mutually cooperate to grasp, seal and divide tubular vessels and vascular tissue. The end effector assembly 100 is rotatable about a longitudinal axis "A" through rotation, either manually or otherwise, of the rotatable assembly 80.

Rotatable assembly 80 generally includes two halves, which, when assembled, form a generally circular rotatable member 82 (as well as other components described herein). An embodiment of a rotatable assembly, such as the rotatable assembly 80 of FIG. 1, in accordance with the present disclosure, is shown in more detail in FIG. 2. It will be understood, however, that other rotatable assembly embodiments may also be used (e.g., 380, 480, 580 and 780 shown in FIGS. 3A, 4A, 5 and 7, respectively).

Forceps 10 may include a switch 200 configured to permit the user to selectively activate the forceps 10 in a variety of different orientations, i.e., multi-oriented activation. In embodiments, when the switch 200 is depressed, electrosurgical energy is transferred to the jaw members 110 and 120. It is envisioned that the switch 200 may be disposed on another part of the forceps 10, e.g., the handle 50, rotatable member 82, housing 20, etc.

Although FIG. 1 depicts a bipolar forceps 10 for use in connection with endoscopic surgical procedures, the teachings of the present disclosure may also apply to more traditional open surgical procedures. For the purposes herein, the forceps 10 is described in terms of an endoscopic instrument. It is contemplated that an open version of the forceps may also include the same or similar operating components and features as described herein.

End effector assembly 100 generally includes a pair of opposing jaw members 110 and 120. Shaft 12 generally includes a distal end 16 configured to mechanically engage the end effector assembly 100, and a proximal end 14 configured to mechanically engage the housing 20. Examples of end effector assembly embodiments, details of how the shaft 12 connects to the end effector 100, as well as details of how the shaft 12 is received within the housing 20 and connections relating thereto, are disclosed in commonly-assigned U.S. Pat. No. 7,150,097 entitled "METHOD OF MANUFACTURING JAW ASSEMBLY FOR VESSEL SEALER AND DIVIDER", the disclosure of which is incorporated herein by reference in its entirety.

In embodiments, the forceps 10 includes an electrosurgical cable 310. Electrosurgical cable 310 may be formed from a suitable flexible, semi-rigid or rigid microwave conductive cable, and may connect directly to an electrosurgical power generating source, e.g., an electrosurgical generator (not shown). The power generating source may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Electrosurgical cable 310 may additionally, or alternatively, provide a conduit (not shown) configured to provide coolant fluid from a coolant source (not shown) to one or more components of the forceps 10. The forceps 10 may alternatively be configured as a wireless device.

It is contemplated that the forceps 10 (and/or an electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of sensor system embodiments are described in commonly-assigned U.S. patent application Ser. No. 10/427,832 entitled "METHOD AND SYSTEM FOR CONTROLLING OUTPUT OF RF MEDICAL GENERATOR" filed on May 1, 2003, the disclosure of which is incorporated herein by reference in its entirety.

The forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of the shaft 12 may be selectively and releasably engageable with the housing 20 and the handle assembly 30. In either of these two instances, the forceps 10 would be considered "partially disposable" or "reposable", e.g., a new or different end effector assembly 100 (or end effector assembly 100 and shaft 12) selectively replaces the old end effector assembly 100 as needed. As can be appreciated, some of the presently-disclosed electrical and/or mechanical connections may have to be altered to modify the instrument to a reposable forceps.

Handle assembly 30 includes a fixed handle 50 and a movable handle 40. In embodiments, the fixed handle 50 is integrally associated with the housing 20 and the handle 40 is movable relative to the fixed handle 50. In embodiments, the rotatable assembly 80 is integrally associated with the housing 20 and is rotatable approximately 180 degrees in both the clockwise and counterclockwise direction about a longitudinal axis "A-A" of rotation.

In embodiments, the housing 20 is formed from two housing halves (not shown). Each half of the housing 20 may include a series of mechanical interfacing components (not shown) configured to matingly engage with a corresponding series of mechanical interfaces (not shown) to align the two housing halves about the inner components and assemblies of the forceps 10. As can be appreciated, the fixed handle 50 takes shape upon the assembly of the housing halves. It is contemplated that the housing halves (as well as other components described herein) may be assembled together with the aid of alignment pins, snap-like interfaces, tongue and groove interfaces, locking tabs, adhesive ports, etc., utilized either alone or in combination for assembly purposes. Examples of housing embodiments and connections relating thereto are disclosed in the above-mentioned, commonly-assigned U.S. Pat. No. 7,150,097.

Figure 2:
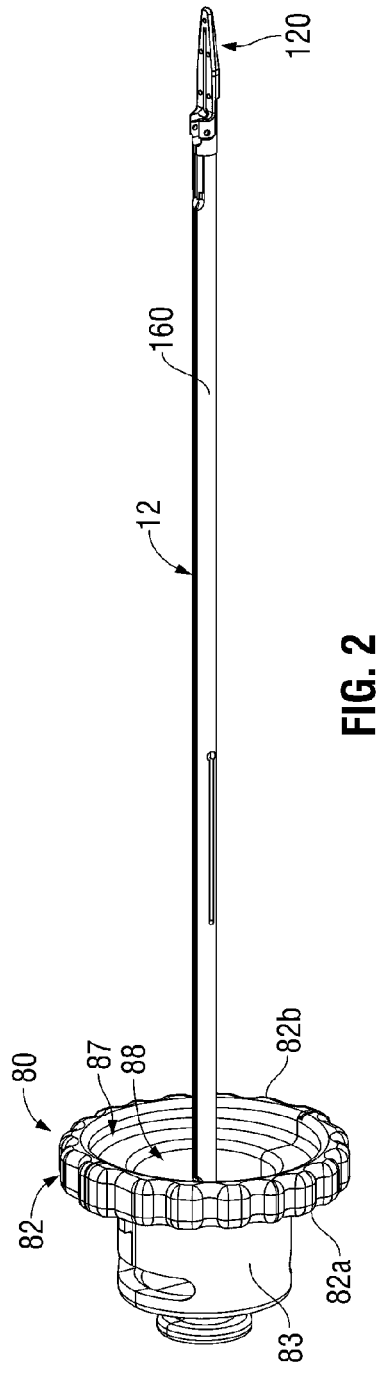
FIG. 2 is an enlarged, perspective view of a rotatable assembly including the rotatable member and shaft of the forceps shown in FIG. 1 according to an embodiment of the present disclosure.

FIG. 2 shows an embodiment of the rotatable assembly 80 in accordance with the present disclosure that includes a rotatable tube 160 and a generally circular rotatable member 82. The rotatable member 82 includes inner surfaces defining an interior space 87 within the rotatable member 82. The rotatable member 82 includes two generally C-shaped halves 82a and 82b, which, when assembled about the tube 160, define an opening in the rotatable assembly 80. The jaw member 120 is designed to be fixed to the end of the rotatable tube 160, which is part of the shaft 12, such that rotation of the tube 160 will impart rotation to the end effector assembly 100 (shown in FIG. 1).

Rotatable assembly 80 includes a hollow body 83 coupled to and extending proximally from the rotatable member 82. Additionally, or alternatively, the rotatable assembly 80 may include a hollow body coupled to and extending distally from the rotatable member 82. Hollow body 83 may take a variety of shapes, e.g., a substantially cylindrical shape. An interior space 87 defined by the rotatable member 82 is in communication with an interior space 88 defined by the hollow body 83. Rotatable assembly 80 is configured to house one or more shaped PCBs within the interior space 87 defined by the rotatable member 82 and/or within the interior space 88 defined by the hollow body 83.

The rotatable assembly 80, or portions thereof, may be configured to house a drive assembly and/or a knife assembly, or components thereof. Hollow body 83 defines an interior space 88, in which components of a drive assembly and/or a knife assembly (or other components) may be accommodated, entirely or in part. Examples of drive assembly embodiments and knife assembly embodiments of the forceps 10 are described in the above-mentioned, commonly-assigned U.S. Pat. No. 7,150,097.

Figure 3B:
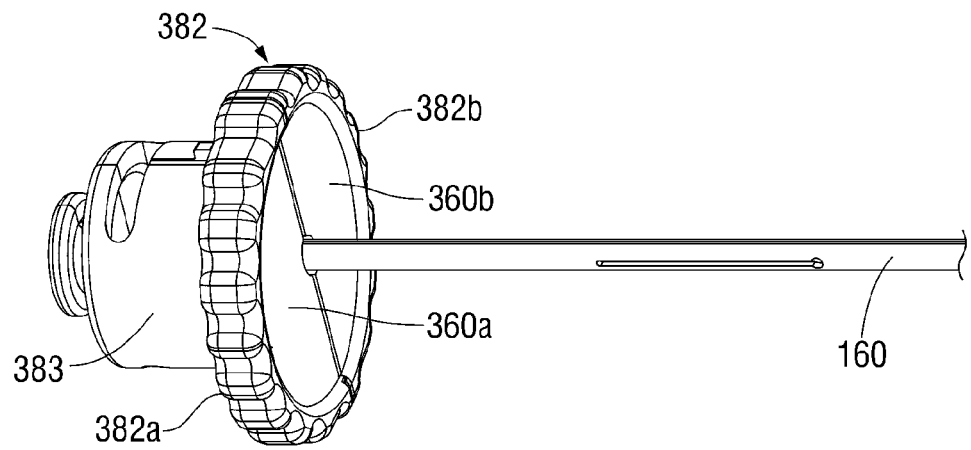
FIG. 3B is an enlarged, perspective, assembled view of the rotatable assembly shown in FIG. 3A according to an embodiment of the present disclosure
Figure 3C:
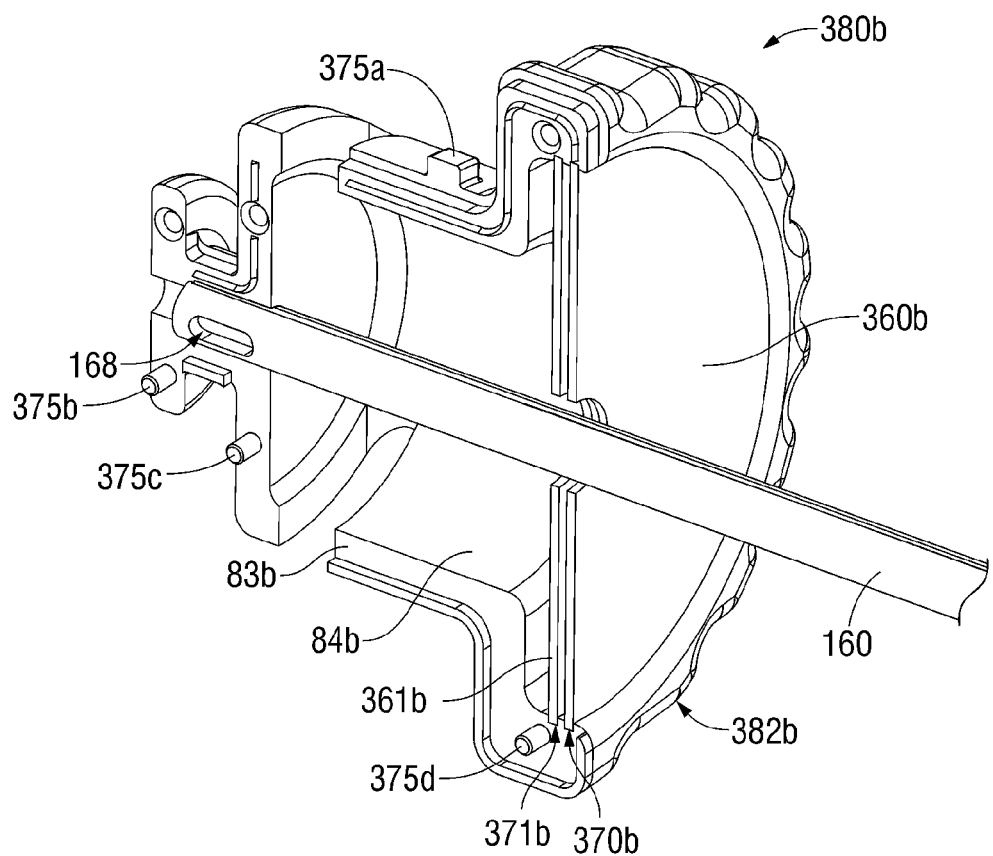
FIG. 3C is an enlarged, perspective, partially-assembled view of the rotatable assembly shown in FIG. 3A according to an embodiment of the present disclosure.

FIGS. 3A through 3C show a rotatable assembly 380 according to an embodiment of the present disclosure that includes a first portion 380a and a second portion 380b, which, when assembled about the tube 160, form the rotatable assembly 380. The proximal end portion of the tube 160 includes a laterally-oriented slot 168, which is designed to interface with the rotatable assembly 380 as described below.

Rotatable assembly 380 includes a rotatable member 382, and may include a hollow body 383 coupled to and extending proximally from the rotatable member 382, e.g., as shown in FIG. 3B. Rotatable assembly 380 is configured to house one or more shaped PCBs within the interior space defined by inner surfaces (e.g., 74a and 74b shown in FIG. 3A) of the rotatable member 382 and/or within the interior space defined by inner surfaces (e.g., 84a and 84b shown in FIG. 3A) of the hollow body 383. Rotatable assembly 380 includes a plurality of grooves, e.g., 370a, 370b, 371a and 371b, recessed into inner surfaces, e.g., 74a and 74b, of the rotatable member 382 and configured to receive therein a peripheral edge portion of one or more shaped PCBs. The shaped PCBs may have a generally circular shape, a generally half-circular shape, or other shapes (e.g., PCB 1065 shown in 10).

Second portion 380b of the rotatable assembly 380 may include a series of mechanical interfaces, e.g., detents/flanges 375a, 375b, 375c and 375d shown in FIGS. 3A and 3C, which generally matingly engage a corresponding series of sockets or other mechanical interfaces in the first portion 380a to form the rotatable assembly 380. Second portion 380b includes a tab 89b, which together with a corresponding tab 89a (phantomly illustrated in FIG. 3A) disposed on the first portion 380a cooperate to matingly engage the slot 168 formed in the tube 160. As can be appreciated, this permits selective rotation of the tube 160 about a longitudinal axis "A-A" of the shaft 12 by manipulating the rotatable member 382 in the clockwise or counterclockwise direction.

In the embodiment illustrated in FIGS. 3A through 3C, the rotatable assembly 380 is configured to house four, generally half circular-shaped PCBs, 360a, 360b, 361a and 361b, which are aligned with respect to one another about the tube 160 a form two, generally circular-shaped (split) PCBs. The first, second, third and fourth PCBs 360a, 360b, 361a and 361b, respectively, include a curved peripheral edge portion 364a, 364b, 365a and 365b, respectively, and a generally C-shaped opening "O" having a radius larger than the radius of the tube 160. The shape, size and relative positions of the first, second, third and fourth PCBs 360a, 360b, 361a and 361b, respectively, may be varied from the configuration depicted in FIG. 3A.

As cooperatively shown in FIGS. 3A and 3B, the first portion 380a of the rotatable assembly 380 includes a first rotatable-member portion 382a, and the second portion 380b of the rotatable assembly 380 includes a second rotatable-member portion 382b, which, when assembled about the tube 160, form a generally circular rotatable member 382. First portion 380a of the rotatable assembly 380 includes a first hollow-body portion 383a, and the second portion 380b of the rotatable assembly 380 includes a second hollow-body portion 383b, which, when assembled about the tube 160, form a hollow body 383 (shown in FIG. 3B) coupled to and extending proximally from the rotatable member 382.

First rotatable-member portion 382a includes a first groove 370a and a second groove 371a defined therein, and the second rotatable-member portion 382b includes a third groove 370b and a fourth groove 371b. First groove 370a is configured to receive a peripheral edge portion 364a of the first PCB 360a, the second groove 371a is configured to receive a peripheral edge portion 365a of the third PCB 361a, the third groove 370b is configured to receive a peripheral edge portion 364b of the second PCB 360b, and the fourth groove 371b is configured to receive a peripheral edge portion 365b of the fourth PCB 361b. The first, second, third and fourth grooves 370a, 371a, 370b and 371b, respectively, may be provided with a suitable adhesive material for affixing permanently or releasably the generally half circular-shaped PCBs. Providing generally half circular-shaped PCBs (e.g., 360a, 360b, 361a and 361b) to the first rotatable-member portion 382a and the second rotatable-member portion 382b, according to embodiments of the present disclosure, may allow for modularity in the design of the rotatable assembly 380, e.g., by allowing the first rotatable-member portion 382a and the second rotatable-member portion 382b to accommodate various configurations of PCBs, and/or may allow for ease of assembly of the first rotatable-member portion 382a and the second rotatable-member portion 382b about the tube 160.

FIG. 3C shows an embodiment of the second portion 380b of the rotatable assembly 380 in accordance with the present disclosure that includes the second and fourth PCBs 360b and 361b, respectively, with edge portions thereof disposed in the third and fourth grooves 370b and 371b, respectively. The shape, size and relative positions of the first, second, third and fourth grooves 370a, 370b, 371a and 371b, respectively, may be varied from the configuration depicted in FIGS. 3A and 3C.

Figure 4A:
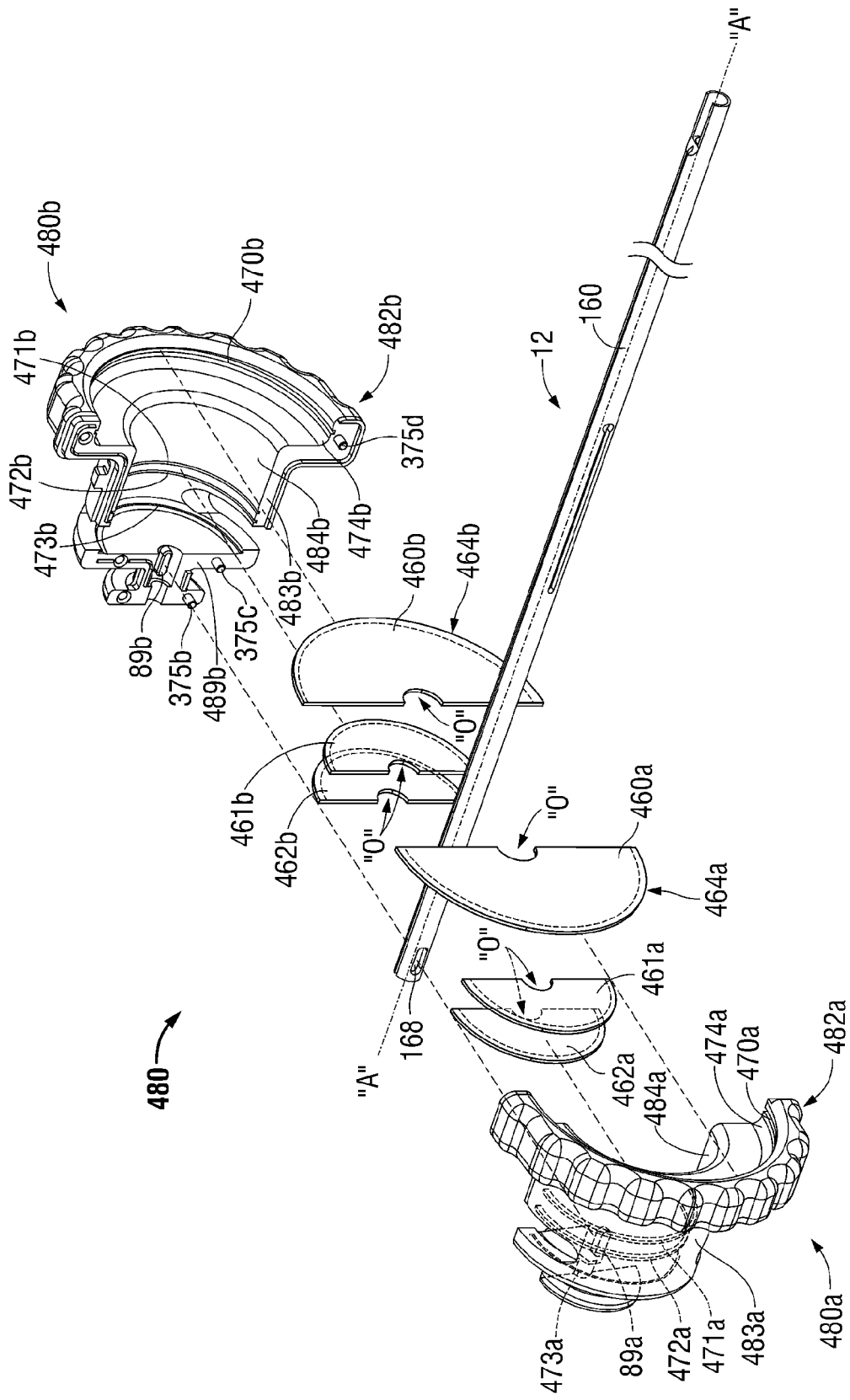
FIG. 4A is an enlarged, perspective view of a rotatable assembly with parts separated according to another embodiment of the present disclosure.
Figure 4B:
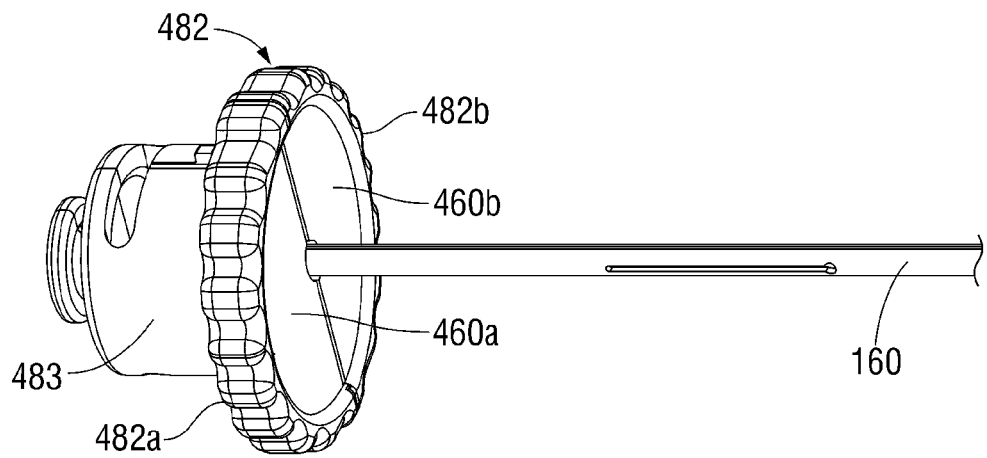
FIG. 4B is an enlarged, perspective, assembled view of the rotatable assembly shown in FIG. 3A according to an embodiment of the present disclosure
Figure 4C:
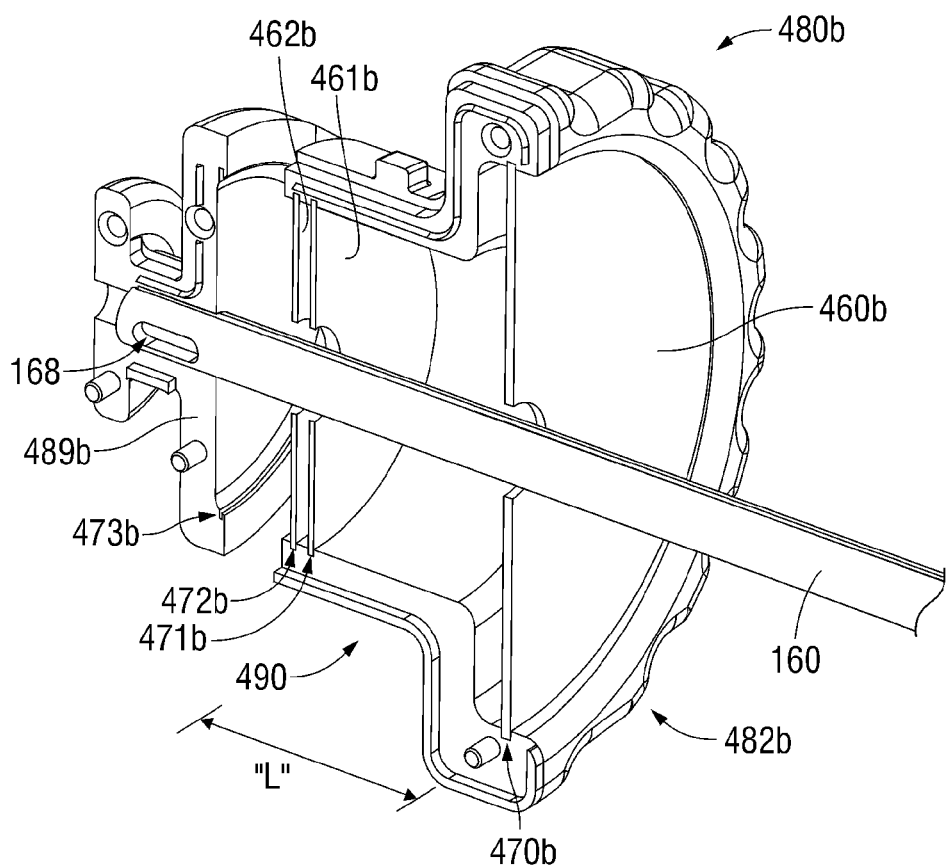
FIG. 4C is an enlarged, perspective, partially-assembled view of the rotatable assembly shown in FIG. 4A according to an embodiment of the present disclosure.

FIGS. 4A through 4C show a rotatable assembly 480 according to another embodiment of the present disclosure that includes a rotatable member 482 and a hollow body 483 coupled to and extending proximally from the rotatable member 482. Rotatable assembly 480 includes a first portion 480a and a second portion 480b, which, when assembled about the tube 160, form the rotatable assembly 480. First portion 480a and the second portion 480b of the rotatable assembly 480 are similar to the first portion 380a and the second portion 380b, respectively, of the rotatable assembly 380 shown in FIG. 3A, except for the grooves in the inner surfaces 484a and 484b of the hollow body 483 and the inner surfaces 474a and 474b of the rotatable member 482.

First portion 480a of the rotatable assembly 480 includes a first rotatable-member portion 482a, and the second portion 480b of the rotatable assembly 480 includes a second rotatable-member portion 482b, which, when assembled about the tube 160, form the generally circular rotatable member 482. First portion 480a of the rotatable assembly 480 includes a first hollow-body portion 483a, and the second portion 480b of the rotatable assembly 480 includes a second hollow-body portion 483b, which, when assembled about the tube 160, form the hollow body 483. As shown in FIG. 4A, the rotatable assembly 480 may be configured to house one or more shaped PCBs within the interior space defined by inner surfaces 474a and 474b of the rotatable member 482 and within the interior space defined by inner surfaces 484a and 484b of the hollow body 483.

Rotatable member 482 is configured to house one or more generally circular-shaped PCBs or generally half circular-shaped PCBs (e.g., 460a and 460B), and the hollow body 483 is configured to house one or more generally circular-shaped PCBs or generally half circular-shaped PCBs (e.g., 461a, 461b, 462a and 462b).

Rotatable assembly 480 according to one embodiment includes six, generally half circular-shaped PCBs 460a, 460b, 461a, 461b, 462a and 462b, which are aligned with respect to one another about the tube 160 to form three, generally circular-shaped (split) PCBs. In embodiments, the PCBs 460a, 460b, 461a, 461b, 462a and 462b include a curved peripheral edge portion (e.g., 464a and 464b shown in FIG. 4A) and a generally C-shaped opening "O" having a radius larger than the radius of the tube 160. The shape, size and relative positions of the PCBs 460a, 460b, 461a, 461b, 462a and 462b may be varied from the configuration depicted in FIG. 4A.

In the embodiment illustrated in FIGS. 4A through 4C, the rotatable member 482 is provided with two grooves 470a and 470b configured to receive a peripheral edge portion 465a and 464b, respectively, of two, generally half circular-shaped PCBs 460a and 460b, respectively, and the hollow body 483 is provided with four grooves 471a, 471b, 472a and 472b configured to receive a peripheral edge portion of four, generally half circular-shaped PCBs 461a, 461b, 462a and 462b, respectively. Hollow body 483 may be provided with additional grooves (e.g., 473a and 474a) for receiving one or more additional PCBs (not shown), which may be used to offer additional functionality. The shape, size and relative locations of the grooves 470a, 470b, 471a, 471b, 472a and 472b may be varied from the configuration depicted in FIGS. 4A and 4C. Although six grooves are shown in FIG. 4A, it is to be understood that any various numbers of grooves (and/or slots, pockets, channels or other recesses) may be utilized.

Rotatable assembly 480 includes a wall 489 disposed at the proximal end of the hollow body 483. As best illustrated in FIG. 4C, PCBs located within the hollow body 483 may be disposed in a proximal portion of the hollow body 483, e.g., in relatively close proximity to the wall 489. In embodiments, one or more PCBs may be disposed in a proximal portion of the hollow body 483, and spaced apart, by a length "L", from PCBs located within the rotatable member 482, defining an interior cavity 490. Length "L" may be any suitable length. Length "L" may be selected so that the interior cavity 490 is utilizable to house a drive assembly and/or a knife assembly, or components thereof.

Figure 5:
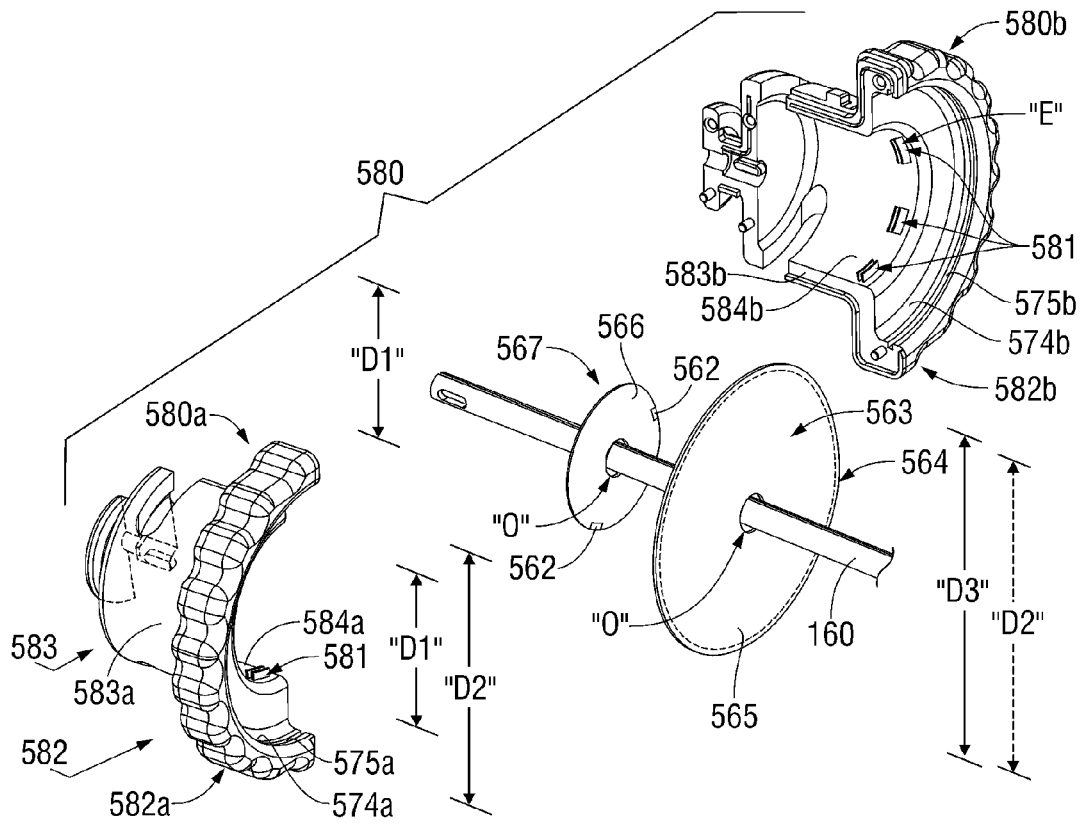
FIG. 5 is an enlarged, perspective view of a rotatable assembly with parts separated according to yet another embodiment of the present disclosure.
Figure 6:
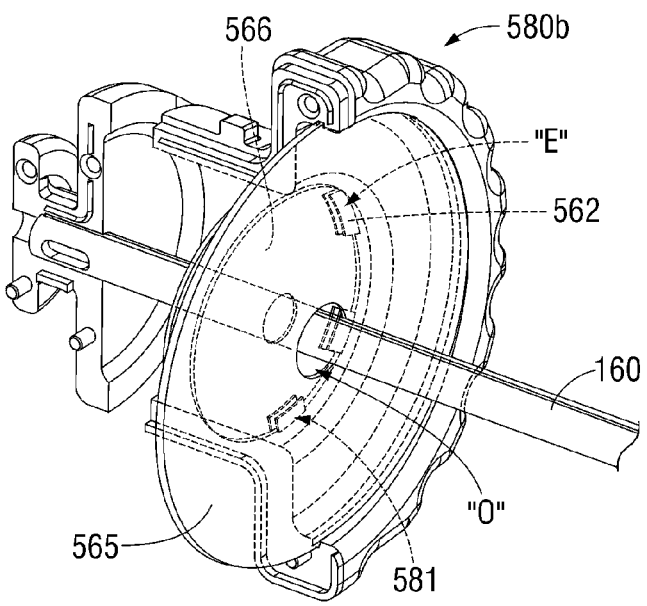
FIG. 6 is an enlarged, perspective view of an assembled portion of the rotatable assembly shown in FIG. 5 according to an embodiment of the present disclosure.

FIGS. 5 and 6 show a rotatable assembly 580 according to another embodiment of the present disclosure that includes a first portion 580a and a second portion 580b, which, when assembled about the tube 160, form the rotatable assembly 580. Rotatable assembly 580 according to various embodiments is configured to house one or more shaped PCBs.

First portion 580a of the rotatable assembly 580 includes a first rotatable-member portion 582a and a first hollow-body portion 583a, and the second portion 580b of the rotatable assembly 580 includes a second rotatable-member portion 582b and a second hollow-body portion 583b. Inner surfaces of the first rotatable-member portion 582a and/or the second rotatable-member portion 582b may include one or more grooves, slots, pockets, channels or other recesses configured to receive at least portions of a shaped PCB. Additionally, or alternatively, inner surfaces of the first hollow-body portion 583a and/or the second hollow-body portion 583b may include one or more grooves (e.g., 471a, 471b, 472a and 472b shown in FIG. 4A), slots, pockets, channels or other recesses configured to receive at least portions of a shaped PCB.

Inner surfaces of the first hollow-body portion 583a and the second hollow-body portion 583b may be provided with one or more receptacle assemblies 581 configured to receive at least portions of a PCB. The presently-disclosed receptacle assemblies 581 may be configured to include an electrical connector part "E" adapted to provide electrical connection to a PCB.

First rotatable-member portion 582a and the second rotatable-member portion 582b, when assembled about the tube 160, form a rotatable member 582. Inner surfaces 574a and 574b of the rotatable member 582 generally define a chamber, or interior cavity, having a diameter "D2". First hollow-body portion 583a and the second hollow-body portion 583b, when assembled about the tube 160, form a hollow body 583 coupled to and extending proximally from the rotatable member 582. Inner surfaces 584a and 584b of the hollow body 583 generally define a chamber, or interior cavity, having a diameter "D1".

In the embodiment illustrated in FIGS. 5 and 6, the rotatable assembly 580 includes two, generally circular-shaped PCBs 565 and 566, which include a generally circular-shaped opening "O" having a diameter larger than the diameter of the tube 160. The shape, size and relative positions of the PCBs 565 and 566 may be varied from the configuration depicted in FIGS. 5 and 6.

First PCB 565 generally includes an outer diameter "D3" and an inner diameter "D2". The inner diameter "D2" is indicated by the dashed circle in FIG. 5. An interior region 563 of the PCB 565 is defined by the inner diameter "D2" and the opening "O". An outer peripheral edge portion 564 surrounding the interior region 563 is defined between the outer and inner diameters "D3" and "D2", respectively.

First rotatable-member portion 582a includes a first groove 575a and the second rotatable-member portion 582b includes a second groove 575b. As cooperatively shown in FIGS. 5 and 6, the first groove 575a and the second groove 575b are configured to receive the peripheral edge portion 564 of the first PCB 565.

Second PCB 566 according to embodiments includes an outer diameter "D1" and an outer diametrical edge 567, and may include one or more electrically-conductive portions 562, e.g., metal pads, disposed along the outer diametrical edge 567. In embodiments, the receptacle assemblies 581 are configured to receive at least portions of the second PCB 566, and may be configured to include electrical connector parts "E" adapted to provide electrical connection to electrically-conductive portions 562 of the second PCB 566.

Electrically-conductive portions 562 may be configured to align with and electrically connect with the electrical connector parts "E" of the receptacle assemblies 581 disposed within, or otherwise associated with, the hollow body 583 and/or the rotatable member 582. The electrically-conductive portions 562 may be used as grounding pads, or for electrically interconnecting circuit members, e.g., PCBs, and/or for providing electrical connection to and between electrical components.

Figure 7:
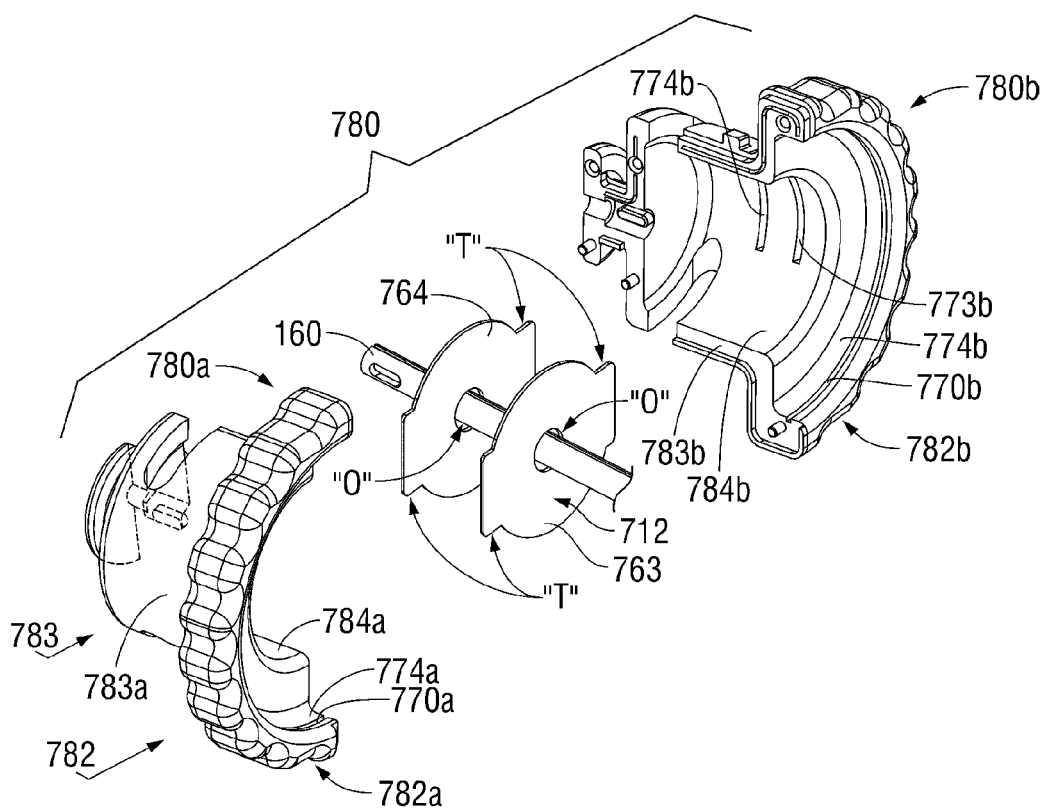
FIG. 7 is an enlarged, perspective view of a rotatable assembly with parts separated according to still another embodiment of the present disclosure.
Figure 8:
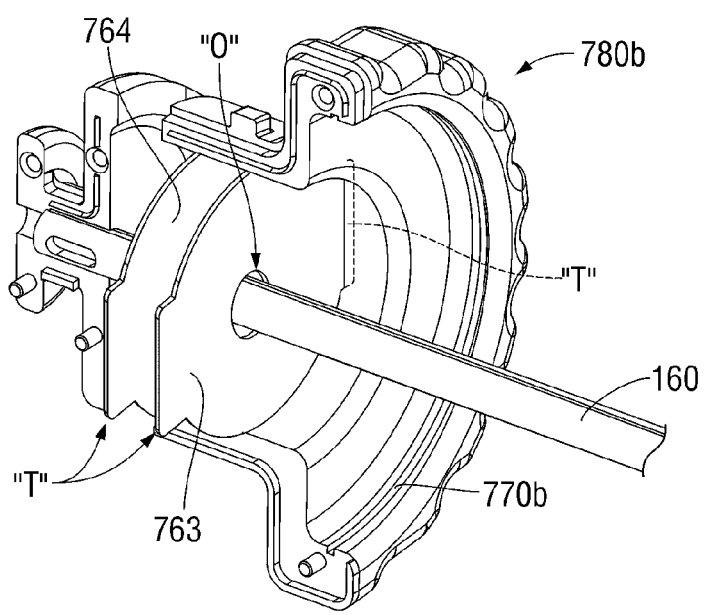
FIG. 8 is an enlarged, perspective view of an assembled portion of the rotatable assembly shown in FIG. 7 according to an embodiment of the present disclosure.

FIGS. 7 and 8 show a rotatable assembly 780 according to an embodiment of the present disclosure that includes a first portion 780a and a second portion 780b, which, when assembled about the tube 160, form the rotatable assembly 780. Rotatable assembly 780 according to various embodiments is configured to house one or more shaped PCBs.

The first portion 780a of the rotatable assembly 780 includes a first rotatable-member portion 782a, and the second portion 780b of the rotatable assembly 780 includes a second rotatable-member portion 782b, which, when assembled about the tube 160, form rotatable member 782. The presently-disclosed rotatable member 782 according to various embodiments may be configured to house one or more generally circular-shaped PCBs or generally half circular-shaped PCBs. As illustrated in FIG. 7, the inner surfaces 774a and 774b of the rotatable member 782 may include a first groove 770a and a second groove 770b, respectively. Rotatable member 782 is similar to the rotatable member 582 shown in FIG. 5, and further description thereof is omitted in the interests of brevity.

First portion 780a of the rotatable assembly 780 includes a first hollow-body portion 783a, and the second portion 780b of the rotatable assembly 780 includes a second hollow-body portion 783b, which, when assembled about the tube 160, form a hollow body 783. In the embodiment illustrated in FIGS. 7 and 8, the hollow body 483 is configured to house two, shaped PCBs 763 and 764.

PCBs 763 and 764 include a generally circular-shaped opening "O" having a diameter larger than the diameter of the tube 160. PCBs 763 and 764 according to embodiments include two tab portions "T" protruding from opposite sides of a generally circular-shaped interior portion 712.

Inner surfaces 784a and 784b of the first hollow-body portion 783a and the second hollow-body portion 783b, respectively, are provided with slots or channels (e.g., 773b and 774b shown in FIG. 7) configured to receive therein the tab portions "T" of the PCBs 763 and 764. The shape and size of the tab portions "T" and the slots or channels for engagement with the tab portions "T" may be varied from the configuration depicted in FIGS. 7 and 8.

One or more grooves may additionally, or alternatively be provided to the inner surfaces 784a and 784b of the hollow body 783 and configured to receive therein portions of one or more generally circular-shaped PCBs and/or generally half circular-shaped PCBs (e.g., similar to the grooves 471b and 472b shown in FIG. 4A), and/or one or more slots or channels may be provided to the inner surfaces 774a and 774b of the rotatable member 782 (e.g., similar to the slots or channels 773b and 774b shown in FIG. 7) configured to receive tab portions of PCBs (e.g., similar to the tab portions "T" of the PCBs 763 and 764).

Figure 9:
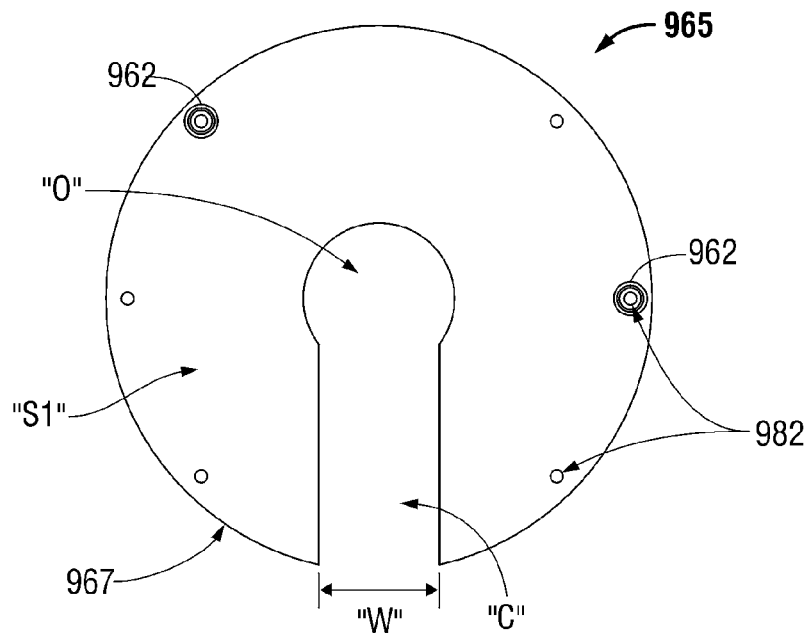
FIG. 9 is a schematic view of shaped printed circuit board according to an embodiment of the present disclosure.

FIG. 9 shows an embodiment of a generally circular-shaped PCB 965 according to the present disclosure that includes an outer diametrical edge 967 and a generally circular-shaped opening "O" having a diameter larger than the diameter of the tube 160. PCB 965 includes a cut-out portion "C" defining a void that extends from the opening "O" to the outer diametrical edge 567. Cut-out portion "C" generally has a width "W" that is larger than the diameter of the tube 160. Cut-out "C" portion is configured to allow the tube 160 to be passed through the cut-out portion "C" into the opening "O" and may allow for ease of installation of the PCB 965 about the tube 160. PCB 965 includes a plurality of fastener holes 982, which may be spaced apart from each other and disposed substantially adjacent to the outer diametrical edge 967.

Figure 11:
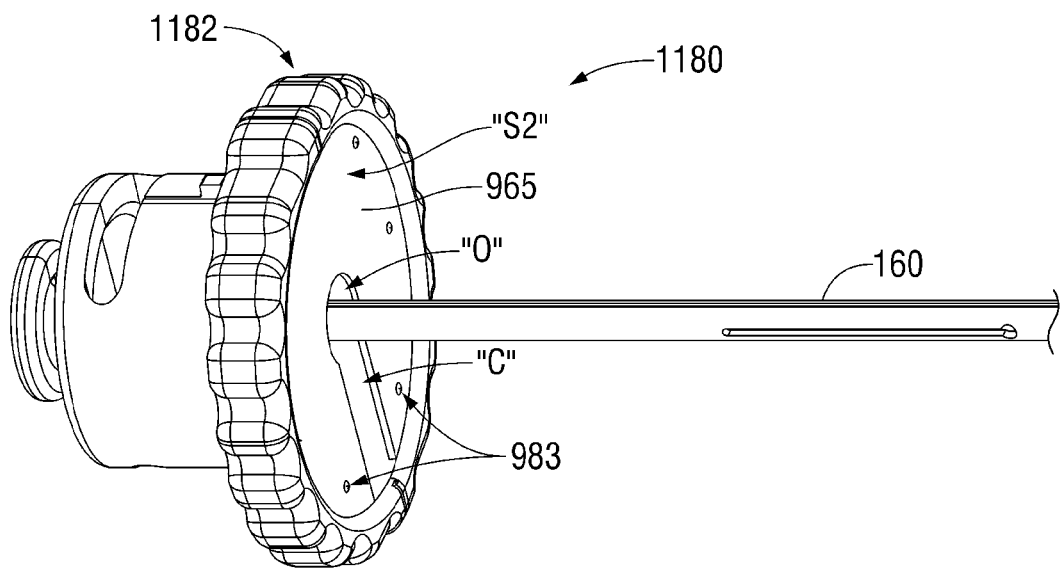
FIG. 11 is an enlarged, perspective view of a rotatable assembly including the printed circuit board shown in FIG. 9 according to an embodiment of the present disclosure.

As cooperatively shown in FIGS. 9 and 11, the PCB 965 generally includes a first surface "S1" and a second surface "S2". PCB 965 may include one or more electrically-conductive portions 962, e.g., metal pads, disposed on the first surface "S1", which may be used as grounding pads, or for electrically interconnecting circuit members, e.g., PCBs, and/or for providing electrical connection to and between electrical components. Electrically-conductive portions 962 may take a variety of shapes and sizes. Electrically-conductive portions 962 may have a ring-like shape, and may be coaxially-disposed about one or more of the fastener holes 982, e.g., as shown in FIG. 9.

Figure 10:
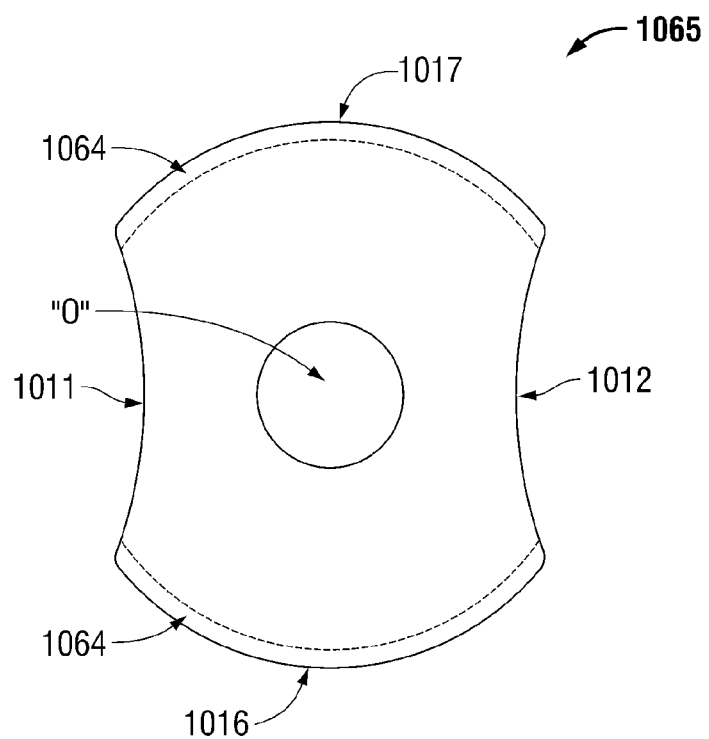
FIG. 10 is a schematic view of another embodiment of a shaped printed circuit board in accordance with the present disclosure.

FIG. 10 shows an embodiment of a shaped PCB 1065 according to the present disclosure that includes two concave-outward edges 1011 and 1012, two concave-inward edges 1016 and 1017, and two peripheral edge portions 1064 associated with the two concave-inward edges 1016 and 1017. The peripheral edge portions 1064 are indicated by the two dashed concave-inward lines in FIG. 10. PCB 1065 includes a generally circular-shaped opening "O" having a diameter larger than the diameter of the tube 160.

Figure 13:
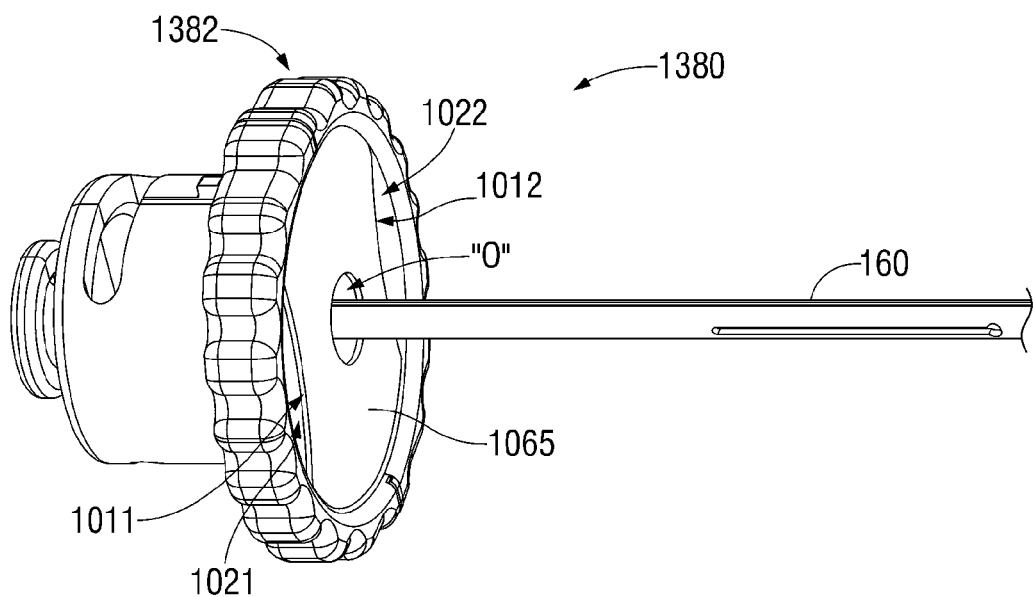
FIG. 13 is an enlarged, perspective view of a rotatable assembly including the printed circuit board shown in FIG. 10 according to an embodiment of the present disclosure.
Figure 14:
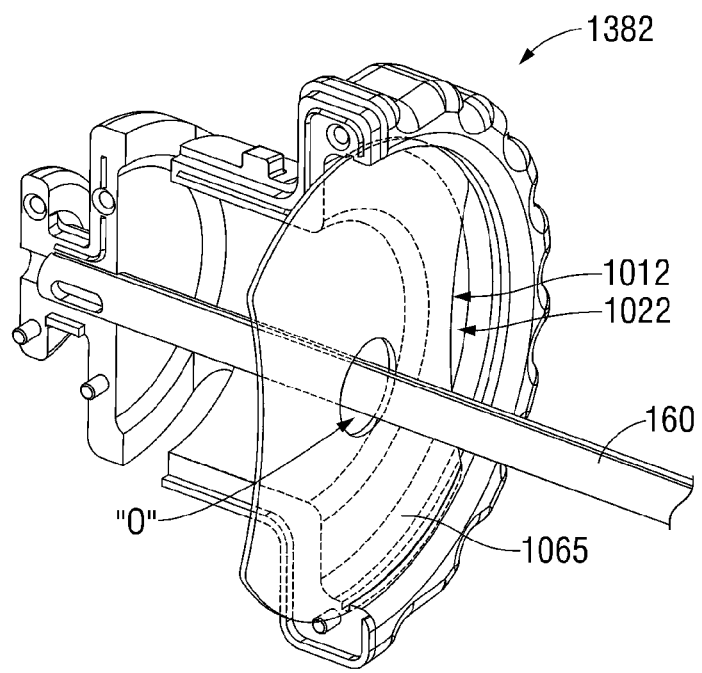
FIG. 14 is an enlarged, perspective view of a portion of the rotatable assembly shown in FIG. 13 according to an embodiment of the present disclosure.

Embodiments of the presently-disclosed rotatable assembly (e.g., 380, 480, 580 and 780 shown in FIGS. 3A, 4A, 5 and 7, respectively) may be configured for receiving the peripheral edge portions 1064 of the shaped PCB 1065 in one or more grooves recessed into inner surfaces of a rotatable member. As illustrated in FIGS. 13 and 14, when the shaped PCB 1065 is housed in an embodiment of the presently-disclosed rotatable member (e.g., 1390 shown in FIG. 13), the concave-outward edges 1011 and 1012 define open spaces (e.g., 1021 and 1022 shown in FIG. 13), which may allow airflow to pass the edges 1011 and 1012 into interior portions of the rotatable assembly, e.g., for cooling electrical components of the PCB 1065 and/or other components. The shape and size of the concave-outward edges 1011 and 1012, the concave-inward edges 1016 and 1017, the peripheral edge portions 1064, and the opening "O" may be varied from the configuration depicted in FIG. 10.

Figure 12:
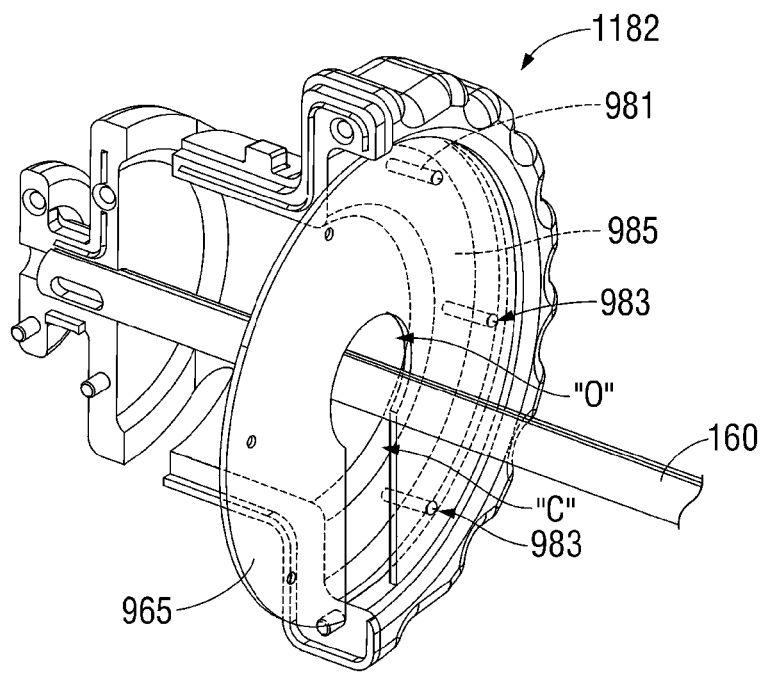
FIG. 12 is an enlarged, perspective view of a portion of the rotatable assembly shown in FIG. 11 according to an embodiment of the present disclosure.

FIG. 11 shows a rotatable assembly 1180 according to another embodiment of the present disclosure that includes a rotatable member 1182 configured to house the PCB 965 shown in FIG. 9. As shown in FIGS. 11 and 12, the interior space defined within the rotatable member 1182 is configured to receive the PCB 965 therein. As best illustrated in FIG. 12, the presently-disclosed rotatable member 1182 according to various embodiments includes a backing member 985.

Shaped PCBs according to the present disclosure (e.g., 965) may be fixedly and/or removably secured to the backing member 985. As shown in FIG. 12, a plurality of support pegs 981 may be disposed on the backing member 985 in a spaced relation corresponding to the pattern of fastener holes 982 of the PCB 965. In embodiments the PCB 965 is coupled to the support pegs 981. As shown in FIGS. 11 and 12, a plurality of fasteners 983 may extend through the fastener holes into the plurality of pegs 983. Fasteners 983 may be any suitable fastener used to fixedly secure the PCB 965 to the support pegs 981. Examples of fasteners that may be suitable for use as the fasteners 983 include pins and threaded fasteners, e.g., screws, which may be formed of metal, plastic or any other suitable material. It will be appreciated that other suitable fasteners may be used such as adhesively-bonded fasteners. In embodiments, the PCB 965 may be removably secured to the support pegs 981.

As mentioned above, the shaft 12 (e.g., shown in FIGS. 1, 2, 3A and 4A) and/or the end effector assembly 100 may be disposable and, therefore, selectively and/or releasably engagable with the housing 20 and the rotating assembly 80 to form a partially disposable forceps 10 and/or the entire forceps 10 may be disposable after use. In embodiments, the PCB 965 may be disposable and, therefore, removable (e.g., removably secured to the support pegs 981 or the backing member 985) from the presently-disclosed rotatable assembly.

FIG. 13 shows a rotatable assembly 1380 according to another embodiment of the present disclosure that includes a rotatable member 1382. Rotatable member 1382 includes one or more grooves (e.g., similar to the grooves 370a, 370b, 371a and 371b shown in FIG. 3) recessed into inner surfaces of the rotatable member 1182 and configured to receive therein a peripheral edge portion of one or more shaped PCBs.

In the embodiment illustrated in FIGS. 13 and 14, the rotatable member 1182 is configured to house the PCB 1065 of FIG. 10. As mentioned above, the concave-outward edges 1011 and 1012 of the PCB define open spaces 1021 and 1022, respectively, which may allow airflow to pass the edges 1011 and 1012 into interior portions of the rotatable assembly 1380, e.g., for cooling electrical components of the PCB 1065 and/or other components housed within the rotatable assembly 1380.

Various embodiments of the presently-disclosed rotatable assembly include a rotatable member configured to house one or more shaped PCBs within an interior space defined by inner surfaces of the rotatable member. The above-described rotatable assembly may include a hollow body configured to house one or more shaped PCBs within an interior space defined by inner surfaces of the hollow body. In embodiments, the hollow body is coupled to the rotatable member and extends proximally and/or distally therefrom.

The above-described rotatable assembly may include one or more receptacle assemblies (e.g., 581 shown in FIG. 5) and/or grooves (e.g., 370a shown in FIG. 3A) and/or slots (e.g., 773b shown in FIG. 7) recessed into, or otherwise associated with, inner surfaces of the rotatable member and/or the hollow body, configured to receive therein portions of the presently-disclosed shaped PCBs. The above-described electrosurgical devices including the presently-disclosed rotatable assembly may be wired or wireless devices.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electrosurgical instrument, comprising:
    a housing having an elongated shaft extending therefrom, the elongated shaft defining a longitudinal axis;
    a rotatable member disposed within the housing configured to rotate with respect to the housing such that the elongated shaft is rotated about the longitudinal axis in response to rotation of the rotatable member, the rotatable member including an inner surface; and
    an electrical component supported by the inner surface, the elongated shaft having a proximal portion secured to the rotatable member proximal of the electrical component.

2. The electrosurgical instrument according to claim 1, wherein the electrical component includes a printed circuit board supported by the inner surface.

3. The electrosurgical instrument according to claim 2, wherein the inner surface defines an inner space that houses the printed circuit board.

4. The electrosurgical instrument according to claim 2, wherein the printed circuit board is half circular-shaped and includes a linear edge orthogonal to the longitudinal axis of the elongated shaft.

5. The electrosurgical instrument according to claim 4, wherein the printed circuit board defines a C-shaped opening on the linear edge that has a radius larger than a radius of the elongated shaft.

6. The electrosurgical instrument according to claim 2, wherein the printed circuit board is circular-shaped.

7. The electrosurgical instrument according to claim 1, wherein the inner surface of the rotatable member defines a groove that receives a peripheral edge portion of the electrical component.

8. The electrosurgical instrument according to claim 1, wherein the electrical component is planar and defines an opening positioned about the elongated shaft.

9. The electrosurgical instrument according to claim 1, wherein a plane defined by the electrical component is transverse to the longitudinal axis of the elongated shaft.

10. The electrosurgical instrument according to claim 1, further comprising a hollow body including an interior surface defining an interior space, the hollow body coupled to the rotatable member such that an inner space defined by the inner surface of the rotatable member is in communication with the interior space defined by the hollow body.

11. The electrosurgical instrument according to claim 10, further comprising a receptacle assembly coupled to the interior surface of the hollow body, the receptacle assembly configured to receive a portion of the electrical component.

12. The electrosurgical instrument according to claim 11, wherein the electrical component includes an outer diametrical edge and an electrically conductive portion disposed along the outer diametrical edge.

13. The electrosurgical instrument according to claim 12, wherein receptacle assembly includes an electrical connector adapted to provide an electrical connection to the electrically conductive portion of the electrical component.

14. The electrosurgical instrument according to claim 1, wherein the housing includes a handle assembly having first and second handles, at least one of the first or second handles moveable relative to the other handle.

15. The electrosurgical instrument according to claim 14, further comprising an end effector coupled to a distal end of the elongated shaft.

16. The electrosurgical instrument according to claim 15, wherein the end effector is actuatable by movement of the first handle relative to the second handle.

17. An electrosurgical instrument, comprising:
    a housing having an elongated shaft extending therefrom, the elongated shaft defining a longitudinal axis;
    a rotatable member disposed on the housing configured to rotate with respect to the housing such that the elongated shaft is rotated about the longitudinal axis in response to rotation of the rotatable member, the rotatable member including an inner surface defining an inner space; and a first printed circuit board disposed within the inner space, the elongated shaft having a proximal portion secured to the rotatable member proximal of the first printed circuit board.

18. The electrosurgical instrument according to claim 17, wherein the first printed circuit board is half circular-shaped and includes a first linear edge orthogonal to the longitudinal axis of the elongated shaft.

19. The electrosurgical instrument according to claim 18, further comprising a second printed circuit board disposed within the inner space defined by the rotatable member, the second printed circuit board being half circular-shaped and including a second linear edge orthogonal to the longitudinal axis of the elongated shaft, the first and second linear edges abutting one another.

20. The electrosurgical instrument according to claim 19, wherein each of the first and second linear edges define a C-shaped opening, the C-shaped openings of the first and second linear edges aligned with one another to define a circular opening about the elongated shaft.

* * * * *